United States Patent [19]

Dybas et al.

[11] 4,362,877
[45] Dec. 7, 1982

[54] 2,4-DISUBSTITUTED-1,2,5-THIADIAZOL-3(2H)-ONE ANTIMICROBIALS

[75] Inventors: Richard A. Dybas, Somerville; Bruce E. Witzel, Rahway; Nathaniel Grier, Englewood, all of N.J.

[73] Assignee: Merck & Co., Inc., Rahway, N.J.

[21] Appl. No.: 142,193

[22] Filed: Apr. 21, 1980

[51] Int. Cl.³ .................. A01N 43/82; C07D 285/10; C07D 405/06
[52] U.S. Cl. .................. 548/135; 424/270; 564/164; 564/165; 564/196; 564/197; 549/493
[58] Field of Search ......................... 548/135

[56] References Cited
U.S. PATENT DOCUMENTS 3,763,176 10/1973 Kohn et al. .................. 548/135
3,854,000 12/1974 Kohn et al. .................. 424/270
4,094,986 6/1978 Rokach et al. ............... 548/135

OTHER PUBLICATIONS

Vaughan et al., J. Am. Chem. Soc., vol. 74, pp. 676–678, (1952), QD1A5.
Bodanszky et al., J. Am. Chem. Soc., vol. 81, pp. 5488–5481, (1959), QD1A5.
Weinstock et al., Advances in Heterocyclic Chemistry, vol. 9, (Katritsky et al., ed., New York, 1968), p. 117, QD400A2.

*Primary Examiner*—Alton D. Rollins
*Attorney, Agent, or Firm*—Raymond M. Speer; Edmunde D. Riedl; Mario A. Monaco

[57] ABSTRACT

2,4-Disubstituted-1,2,5-thiadiazol-3(2H)-one antimicrobials have broad spectrum antibacterial and antifungal activity. They are found to be especially useful in agriculture to protect plants against diseases such as leaf, stem, and fruit spotting, internal discoloration and decay of fruits and vegetables. These compounds are particularly active against diseases caused by the genera Pseudomonas, Xanthomonas, Erwinia, and Corynebacterium.

6 Claims, No Drawings

2,4-DISUBSTITUTED-1,2,5-THIADIAZOL-3(2H)-ONE ANTIMICROBIALS

This invention relates to a new class of antibacterial and antifungal compounds, particularly 2-R,4-R$^1$ disubstituted-1,2,5-thiadiazol-3(2H)-ones. Although derivatives of 1,2,5-thiadiazoles are known, for instance, U.S. Pat. No. 4,094,986 which disclosed 2-substituted-1,2,5-thiadiazole-3(2H)-ones; U.S. Pat. Nos. 3,854,000 and 3,763,176 wherein on the same nucleus a chlorine is substituted in the 4-position, and other analogs free of substituents in the 2-position but having 4-alkyl groups as disclosed in "The 1,2,5-Thiadiazoles" by L. M. Weinstock and P. I. Pollak, p. 117, in "Advances in Heterocyclic Chemistry", vol. 9, A. R. Katritsky and A. J. Boulton, Academic Press, New York (1968), such compounds have significant deficiencies, especially ring instability to hydrolysis.

The 2-R,4-R$^1$-disubstituted 1,2,5-thiadiazol-3(2H)-ones of this invention have the structural formula I:

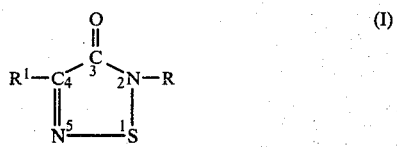

where R is a hydrocarbon group of from 1–18 carbon atoms including C$_1$ to C$_{18}$ alkyl linear or branched; phenyl —C$_1$ to C$_{10}$ alkyl and phenyl; said phenyl groups may be mono- or di-substituted as with bromine, chlorine, fluorine and iodine, with alkyl containing from C$_1$ to C$_{12}$ carbon atoms or with alkoxy having the same number of carbon atoms. R includes, for example, methyl, ethyl, n-propyl, isopropyl, butyl, sec-butyl, t-butyl, pentyl, 1-(2-ethyl)hexyl, octyl, nonyl, decyl, dodecyl, hexadecyl, octadecyl, 4-chlorophenyl, 3,4-dichlorophenyl, 3,4-dibromophenyl, 3-iodophenyl, 4-methoxyphenyl, 3,4-methylenedioxyphenyl, 4-n-dodecyloxyphenyl, phenylmethyl, 4-methoxyphenethyl, 3-(4-methylphenyl)propyl, 4-(3-chlorophenyl)butyl, 12-(4-methoxyphenyl)-n-dodecyl, and tetrahydrofuran-2-ylmethyl; and R$^1$ is an electron-donating group such as C$_1$ to C$_{18}$ alkyl, linear or branched; loweralkoxyalkyl wherein the alkoxy group contains from one to six carbon atoms and the alkyl moiety from one to four carbon atoms, tetrahydrofuran-2-ylmethyl, phenyl-C$_1$ to C$_{10}$ alkyl; ring substituted or disubstituted phenyl- C$_1$–C$_{10}$ alkyl where said substituent is the same or different and said substituent is bromine, chlorine, fluorine or iodine, C$_1$ to C$_{12}$ alkyl or C$_1$ to C$_{12}$ alkoxy.

R$^1$ includes for example, the alkyl groups of R, methoxymethyl, 3-methoxypropyl, 2-ethoxyethyl, n-butoxyethyl, 2,2-dimethylpropoxyethyl, 4-methylpentoxyethyl, 4-n-hexyloxyethyl, 4-methoxybutyl, 4-butoxybutyl and 4-n-hexyloxybutyl.

The compounds of this invention are prepared by reacting an amide of formula II with at least one mole of sulfur monohalide, S$_2$X$_2$, where X is bromine or chlorine.

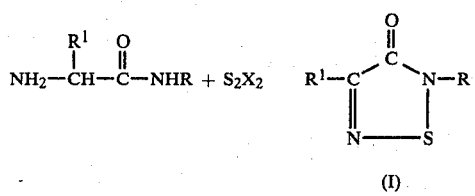

The reation is conducted in an inert solvent such as dimethylformamide or hexamethylphosphotriamide at a temperature of from about −10° to 60° C. for from about 1 to 18 hours.

The molar ratios of R$^1$-substituted glycine R-substituted amide free base or salt to S$_2$X$_2$ can range from 1:2 to 1:5 although a ratio of 1:3 is most satisfactory.

After reaction is complete, the solvent is stripped under vacuum.

The 2-R,4-R$^1$-disubstituted-1,2,5-thiadiazol-3(2H)-ones are essentially neutral compounds, or relatively weak bases depending upon the electron-donating potential of the 4-R$^1$ group, and are readily extractable from basic or weakly acidic mixtures. The products can be purified by distillation, fractional crystallization, or column chromatography by well-known techniques.

The preferred compounds are:
2-(4-Chlorophenylmethyl)-4-methyl-1,2,5-thiadiazol-3(2H)-one
2-(3,4-Dichlorophenylmethyl)-4-methyl-1,2,5-thiadiazol-3(2H)-one
2-Phenyl-4-methyl-1,2,5-thiadiazol-3(2H)-one
2-n-Hexyl-4-methyl-1,2,5-thiadiazol-3(2H)-one
2-n-Propyl-4-(phenylmethyl)-1,2,5-thiadiazol-3(2H)-one
2-n-Propyl-4-(4-chlorophenylmethyl)-1,2,5-thiadiazol-3(2H)-one
2-n-Propyl-4-(3,4-Dichlorophenylmethyl)-1,2,5-thiadiazol-3(2H)-one
2-(4-Chlorophenyl)-4-methyl-1,2,5-thiadiazol-3(2H)-one
2-(4-Chlorophenylmethyl)-4-(tetrahydrofuran-2-ylmethyl)-1,2,5-thiadiazol-3(2H)-one General Method: Reaction of α-amino N-substituted acid amide with sulfur monochloride. Preparation of 2,4-disubstituted-1,2,5-thiadiazol-3(2H)-ones. The α-amino N-substituted amino acid amide (0.1 mole, free base or amine salt) was added to a solution of 24.3 ml (0.3 mole) of sulfur monochloride in 50 ml of DMF, stirred 5 hours at room temperature, and poured into 250 ml of ice water. The mixture was filtered to remove the precipitate sulfur; the filtrate was extracted four times with 100-ml portions of ether or methylene chloride. The combined organic solvent extracts were washed once with a small amount of water, dried over anhydrous sodium sulfate, and evaporated to yield 40–60% of the crude 2,4-disubstituted-1,2,5-thiadiazol-3(2H)-ones. Purification was accomplished by crystallization from preferably non-polar solvents, by column chromatography on silica gel using methylene chloride admixed with minor amounts of more polar solvents, by sublimation under reduced pressure and other well-known methods.

The following examples illustrate the invention but are not to be considered as limitation.

EXAMPLE 1A

2-[(4-Chlorophenyl)methyl]-4-methyl-1,2,5-thiadiazol-3(2H)-one

N-(4-Chlorophenylmethyl)-2-aminopropionamide hydrobromide (powdered) (3.8 g, 0.013 mole) and a solution of sulfur monochloride (3.5 g, 0.026 mole) in 10 ml of dimethylformamide (DMF) were added portionwise simultaneously to 15 ml of DMF kept at 2° C. in an ice bath, with gradual stirring. The concurrent addition took 40 minutes, and the reaction mixture was maintained at 2°-6° C. throughout. The agitated mixture was held at 5° C. for an additional 2 hours and allowed to stand at 20° C. over night. The precipitated sulfur was removed by suction filtration, and the filtrate was poured into 200 ml of ice water. The reaction mixture was extracted with methylene chloride, the organic phase was separated, washed with water and dried over anhydrous sodium sulphate. The solvent was removed under reduced pressure to leave 4.0 g of nearly pure solid product. Passage of a solution in methylene chloride over a column of silica gel, followed by elution with ethyl acetate in methylene chloride (1% by vol.) provides analytically pure compound. $R_F$ 0.54 on $S_iO_2$ developed with 5% ethyl alcohol in methylene chloride.

Analysis calculated for $C_{10}H_9ClN_2OS$: Si, C, 49.89; H, 3.76; Cl, 14.73; N, 11.69; S, 13.34. Found: C, 49.76; H, 3.62; Cl, 14.71; S, 13.39.

EXAMPLE 1B

2-n-Propyl-4-phenylmethyl-1,2,5-thiadiazol-3(2H)-one

N-n-Propyl phenylalaninamide (4.1 g, 0.02 mole free base) was added dropwise over a 15 minute period to a stirred cold solution (+1°→+7° C.) of sulfur monochloride (4.9 ml, 0.06 mole) in 2.5 ml of anhydrous dimethylformamide. Within ten minutes sulfur precipitation began. The mixture was maintained at +1°→+7° C. for one-and-a half hours and then at 20°-22° C. for 16 hours. It was poured into 500 ml of ice water, extracted twice with ether, and the organic phase then washed with water, dried over anhydrous sodium sulfate, and after filtration the ether was removed under reduced pressure. The residual oil, 3.8 g, was dissolved in methylene chloride and chromatographed on a column of silica gel (approx. 300 gms). The product was obtained in analytical purity as a faintly yellow oil, 2.4 g (52% yield). Mass spectral analysis indicated a mol. wt. of 234 (calculated 234.4).

Analysis calculated for $C_{12}H_{14}N_2OS$: C, 61.51; H, 6.02; N, 11.96; S, 13.69. Found: C, 61.37; H, 5.98; N, 11.91; S, 13.92.

The following compounds are prepared according to the procedure from the tabulated substituted amino acid amides:

TABLE I

| N-Substituted-2-aminocarboxamide $\begin{array}{c} R^1 \quad R \\ | \quad\quad | \\ NH_2-CH-CONH \end{array}$ | | 2,4-Disubstituted-1,2,5-thiadiazol-3(2H)-one (4) $\begin{array}{c} -C-\!\!\!-\!\!\!-C=O \\ \| \quad\quad | \\ N\diagdown_S\diagup N-(2) \end{array}$ |
|---|---|---|
| $R^1$ | R | |
| $CH_3$ | Cl-C₆H₃(Cl)- (3,4-dichlorophenyl) | 2-(3,4-Dichlorophenylmethyl)-4-methyl |
| $CH_3\!\!>\!\!CH\!\!<\!\!CH_3$ (isopropyl) | C₆H₅- (phenyl) | 2-Phenyl-4-isopropyl |
| n-$C_{12}H_{25}$ | $CH_3$-C₆H₄- | 2-(4-Phenylmethyl)-4-n-dodecyl |
| n-$C_{16}H_{33}$ | methylenedioxyphenyl (3,4-O-CH₂-O-C₆H₃-) | 2-(3,4-Methylenedioxyphenyl)-4-n-hexadecyl |
| $(CH_3)_3C$ | $CH_3O$-C₆H₄-$CH_2CH_2$- | 2-(4-Methoxyphenethyl)-4-t-butyl |
| $CH_3OCH_2$ | Cl-C₆H₄-$CH_2$- | 2-(4-Chlorophenylmethyl)-4-methoxymethyl |
| $C_2H_5OC_2H_4$ | n-$C_6H_{13}$ | 2-n-Hexyl-4-(2-ethoxyethyl) |
| $CH_3OC_3H_6$ | n-$C_3H_7$ | 2-n-Propyl-4-(3-methoxypropyl) |

TABLE I-continued

| N-Substituted-2-aminocarboxamide $\quad$ $R^1$ $\quad$ $R$ $\quad$ $NH_2$—CH—CONH | | 2,4-Disubstituted-1,2,5-thiadiazol-3(2H)-one (4) $\quad$ —C——C=O $\quad$ $\parallel$ $\quad\quad$ $\vert$ $\quad$ N $\quad$ N—(2) $\quad\quad$ $\diagdown$S$\diagup$ |
|---|---|---|
| $R^1$ | $R$ | |
| $CH_3$ |  | 2-(Tetrahydrofuran-2-ylmethyl)-4-methyl |
| 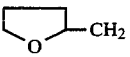 | $CH_3$ | 2-Methyl-4-(tetrahydrofuran-2-ylmethyl) |
| 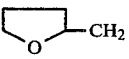 |  | 2-(4-Chlorophenylmethyl)-4-(tetrahydrofuran-2-ylmethyl) |
|  | $CH_3$ | 2-methyl-4-[2-(4-bromophenyl)ethyl] |
| 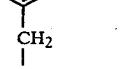 | 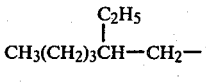 | 2-(2-ethylhexyl)-4-(4-methylphenylethyl) |

The α-amino-N-substituted acid amide intermediates required for the synthesis of the compounds of this invention can be prepared by standard methods, especially from the well-known and readily available commercial α-amino acids. Preferably, the α-amino acids have an amino blocking group such as tertiary-butoxycarbonyl or benzyloxycarbonyl, although p-toluenesulfonyl or trifluoroacetyl are also useful. Other blocking groups are employable and are well-known in the art, especially in the scientific literature relating to peptide synthesis. Amide formation can be obtained from non-blocked amino acids esters by initial preparation of cupric complexes (see S. Yamada, S. Terashima, and M. Wagatsuma, Tetrahedron Letters, No. 18, 1501 (1970)]. A detailed review of methods and reagents for blocking amino groups of amino-carboxylic acids and for deblocking is found in "Protective Groups in Organic Chemistry," J. F. W. McOmie (ed.) Plenum Press, New York (1973), Chapter 2, "Protection of N—H Bonds and NR3" J. W. Barton, p. 43.

Conversion of the N-protected amino-acid to an N-protected mono-substituted carboxamide utilized processes well-known to those skilled in the art. The carboxyl group may be activated as an acyl halide, anhyride, ester, azide or used as a free acid in the presence of a carbodiimide, for example, to react with a primary amine. Or, if the unsubstituted amide is synthesized by reaction with ammonia, then substitution of the amide by alkylation, by exchange reaction with primary amine salts and other known techniques can be employed. An excellent review of these and still other processes for the preparation of N-protected-α-amino-acid monosubstituted carboxamides may be found in "The Chemistry of Amides", J. Zabicky (ed.), Interscience Publishers Div., J. Wiley & Sons, New York (1970); Chapter 2, "The Synthesis of Amides," A. L. J. Beckwith. Deblocking of the protected α-amino group is accomplished by acid or alkaline hydrolysis, by catalytic reduction, cleavage with sodium hydride in refluxing dimethoxyethane, acyl exchange with hydrazine, hydroxylamine, and other applicable methods depending upon the nature of the blocking group and other functional groups of the amino acid amides. α-Amino-ω-alkoxyalkanoic acids are synthesized from sodiophthalimidomalonic ester and alkoxyalkyl halides using base hydrolysis of the resultant alkylated ester to provide acid intermediates which undergo decarboxylation after hydrolysis with mineral acid at 90°–100° C. This procedure is described in U.S. Pat. No. 2,407,203 (Sept. 3, 1946). Tetrahydrofuran-2-yl substituted α-amino acids are prepared from the corresponding furan analogs by catalytic hydrogenation using platinum, e.g. tetrahydrofurylalanine, m.p. 255°–256° from furylalanine [C.A. 24, 2721 (1930)].

EXAMPLE 2

N-(4-Chlorophenylmethyl)-2-aminopropionamide hydrobromide

Step A: N-Benzyloxycarbonylalanine (11.15 g, 0.05 mole) is suspended in 50 ml of $CH_2Cl_2$ and under nitrogen with ice cooling, 7 ml (0.05 mole) of triethylamine is added. The mixture is maintained at 1°–3° C. and with good agitation 5.5 g (4.9 ml, 0.05 mole) of ethyl chloroformate is added dropwise over a 35 minute period. A solution of 4-chlorophenylmethylamine (7.1 g, 0.05 mole) in 12.5 ml of $CH_2Cl_2$ is then added dropwise to the thick suspension over a 40 minute period while maintaining the internal temperature at 1°–3° C. The mixture, after overnight stirring at 20° C., was filtered, the solids taken up in $CH_2Cl_2$, washed with $H_2O$, diluted NaOH, then water, dried over anhydrous sodium sulfate; and the solvent removed by evaporation until crystallization. A yield of 5.5 g was obtained and the product showed one spot, $R_f$ 0.4, on thin layer chromatography using silica gel and 5% ethanol in $CH_2Cl_2$ development.

Step B: A solution of HBr in acetic acid (70 ml, 30–32% by wt) was cooled to 5°–10° C. and with stirring, the product from Step A (5.5 g) was added portionwise over a one-half hour period. The reaction mixture, after complete addition, was stirred an additional hour at the same temperature range and then gradually warmed to 20° C. The solution after 20 hours at 20° C. was mixed with 400 ml of ether, and the precipitated solids were removed by filtration, followed by an ether wash and than air-dried. A yield of 3.18 gm of pure N-(4-chlorophenylmethyl)-2-aminopropionamide hydrobromide was obtained; $R_f$ 0.64, tlc on $S_iO_2$ with development by Si chloroform, conc. aqueous ammonium hydroxide:methanol, 75:5:20 volume percent.

Similarly, by substituting amines or hydrohalide salts thereof, of 3,4-dichlorophenylmethylamine, benzeneamine, 4-methylbenzeneamine, 3,4-methylenedioxybenzeneamine, 4-methoxyphenylethylamine, n-hexylamine, n-propylamine and 4-bromophenylmethylamine for the 4-chlorophenylmethylamine in the Example 2, Step A, the corresponding N-substituted 2-aminopropionamide hydrohalide salt intermediate derivatives are obtained. Also, replacement of the N-benzyloxycarbonylalanine with 2-benzyloxycarbonylamino-3-methylbutyric acid, -n-tetradecanoic acid, -n-octadecanoic acid, -3,3-dimethylbutyric acid, -3-methoxypropionic acid, -4-ethoxybutyric acid, and 5-methoxyvaleric acid and the corresponding amines of Table 1 provides the N-substituted 2-aminocarboxamide required intermediates for the 2,4-disubstituted-1,2,5-thiadiazol-3(2H)-ones listed therein.

Surprisingly, the introduction of an electron-donating group at the 4-position of a 2-substituted-1,2,5-thiadiazol-3(2H)-one imparted relatively high ring stability to hydrolysis when compared to the known 2,4-disubstituted-1,2,5-thiadiazol-3(2H)-ones, namely, the 4-chloro derivatives. Solutions of these compounds were prepared using equal volumes of methanol-aqueous phosphate buffer (pH 8), and decomposition by cleavage of the heterocyclic ring was monitored using ultraviolet absorption changes with time. The following was obtained:

$$R^1 \underset{N \diagdown S \diagup N-R}{\overset{\phantom{xx}=O}{\rule{2cm}{0.4pt}}}$$

| Compound | | % Compound Remaining after Time, hr. | | | | | |
|---|---|---|---|---|---|---|---|
| $R^1$ | R | 0 | 1 | 16 | 48 | 165 | 336 |
| Cl | $CH_2$–⟨O⟩ | 100 | 48 | 6 | 0 | — | — |
| Cl | $CH_2$–⟨O⟩–Cl | 100 | not measured | 0 | 0 | — | — |
| n-$C_3H_7$ | $CH_2$–⟨O⟩ | 100 | 100 | 100 | 100 | 90 | 90 |
| $CH_3$ | $CH_2$–⟨O⟩–Cl | 100 | 100 | 100 | 97 | 93 | 91 |
| $CH_3$ | n-$C_6H_{13}$ | 100 | 100 | 100 | 100 | 100 | 99 |
| H | $CH_2$–⟨O⟩ | 100 | 100 | 96 | 80 | 50 | 26 |

The stability parameter is of major importance for commercial utilization, especially as agricultural antimicrobial agents. Non-systemic plant protectants are applied usually by spraying or dusting. The inhibition or destruction period against phytopathogens must be maintained by the applied products over two weeks or more for adequate control. More frequent crop treatment would be economically prohibitive for practically all kinds of horticulture. More surprisingly, the mechanism of action for 1,2,5-thiadiazol-3(2H)-one type antimicrobials was postulated as ring opening and covalent bonding to nucleophilic moieties of microbial systems; stable rings were considered to cause loss of efficiency. The broad antimicrobial spectrum and high potencies of the compounds of this invention suggest otherwise. One theory may be that stable ring derivatives may be opened by catalysts intracellularly to provide inhibition or cidal action by covalent binding to essential microbial constituents.

The potencies are exemplified with 2-(4-chlorophenylmethyl)-4-methyl-1,2,5-thiadiazol-3(2H)-one for a wide variety of phytopathogens of economic importance. The in vitro assays were run in nutrient agar medium to which various concentrations of compound were added, and after appropriate incubation times and temperature, petri plates were noted which were devoid of fungal growths. The minimal inhibitory concentration (MIC) of compound required was thus obtained:

| Fungus | MIC mcg/ml |
|---|---|
| *Alternaria citri* MF 2970 | 4 |
| *Aspergillus niger* MF 11 | 4 |
| *Botrytis cinerea* MF 4803 | 1 |
| *Cercospora beticola* MF 4571 | 1 |
| *Cladosporium Fulvum* MF 3238 | 1 |
| *Colletotrichum lagenarium* MF 4800 | 2 |
| *Diaperthe phaseolorum* MF 4668 | 0.4 |
| *Fusarium oxysporum* MF 3413 | 4 |
| *Helminthosporium oryzae* MF 4806 | 1 |
| *Helminthosporium maydis* MF 4775 | 0.4 |
| *Monilia nigra* MF 3084 | 2 |
| *Penicillium digitatum* MF 4590 | 4 |
| *Piricularia oryzae* MF 4805 | 0.4 |
| *Phytophthora cambivora* MF 3753 | 2 |

| Fungus | MIC mcg/ml |
| --- | --- |
| Rhizoctonia solani MF 4579 | 8 |
| Sclerotinia sclerotiorum MF 4739 | 0.8 |
| Thielaviopsis basicola MF 3147 | 4 |
| Verticillium dahliae MF 2416 | 4 |

Similarly, high broad spectrum efficiency was found with bacteria responsible for plant diseases. In vitro tests against such fungi as *Uromyces phaseoli* (Bean Rust) and *Helminthosporium oryzae* (Rice spot) in a greenhouse indicated the above 1,2,5-thiadiazoles-3(2H)-one and other 2,4-disubstituted derivatives of this invention protected plants when administered as a single foliar spray for at least seven to fourteen days at practical concentrations of less than 300 mcg/ml.

The compounds of this invention are broad spectrum antibacterial and antifungal agents. For use, the compounds described herein can be applied neat or employed in a diluted form. Satisfactory diluents include any inert material not destructive of the antimicrobial activity and especially liquid formulations comprising aqueous dispersions, solutions, and emulsions. Solid diluents include talc, corn starch, alumina and diatomaceous earth. The antimicrobial agents of this invention can also be deposed on materials such as natural fibers including paper, cotton, wool and synthetic fibers such as nylon, polypropylene, as well as upon inanimate surfaces including hard surfaces such as wood, glass, metal, tile, rubber, plastic, and porous surfaces such as concrete, leather and the like.

In addition, the compounds described herein can be employed in impounded water, such as ponds or industrially-used water such as papermill water to inhibit growth of undesirable bacteria, fungi, and/or algae at levels as low as 0.5–5 ppm.

In the control of slime-producing microorganisms and algae in recirculating industrial water, particularly cooling operations and especially installations such as cooling towers, the compounds of this invention are usually employed alone, but can also be used in combination with other antimicrobial agents. Concentrations in the recirculating water of as little as $1 \times 10^{-4}\%$ by weight are effective in inhibiting microbial growth. To insure effectiveness, especially against more resistant strains of microorganisms, and also when make-up water is added to replace water lost by evaporation and the like, concentrations of from $1 \times 10^{-4}\%$ to $5 \times 10^{-2}\%$ by weight are most satisfactory. Dosage may be continuous or as intermittent "shock treatment", i.e., addition in a 10–20 minute period every 4–8 hours. They are especially useful against bacteria and fungi responsible for stunting the growth and even destruction of many types of crop-producing plants. In agriculture, severe problems are faced in the raising of cotton, beans, corn and other crops because of the loss of yield per acre due to the action of soilborne fungi on seed and on the roots of the young plants. Control or elimination of these losses can be accomplished by the use of the compounds herein described as soil disinfectants in accordance with the invention. They can also be used for the control of bacterial and fungal diseases on trees and stored crops.

In formulating the compounds of this invention for the above uses, these compounds can be employed in combination with other antimicrobial agents, surfactants, insecticides, defoamers and odorants.

Wettable powder formulations for use as a dispersant in water represent a practical means for good distribution in soil. Other methods of achieving the same results include the preparation of dusts. All of the thiadiazol-3(2H)-ones can be blended as fine powders with the commonly used powder diluents such as talc, clay refined silicates, wood flour, sand, magnesium oxide, calcium carbonate, fuller's earth, kaolin, diatomaceous earth, mica, pumice and the like. The powder can have the following formulation:

|  | Percent |
| --- | --- |
| 2,4-Di-substituted-1,2,5-thiadiazol-3(2H)-one | 1–75 |
| Inert Diluent (clay, talc, etc.) | 25–99 |

The mixtures may be finely powdered, e.g., to the 1–10 micron average particle size, or be made by blending the already finely powdered ingredients.

For application as agricultural disinfectants the dusts may be applied to the seed and surrounding soil at the time of planting. The concentration of the sterilant is adjusted to give an effective, nonphytotoxic dosage in the soil. In general, the soil concentration should be from 10 to 25 parts per million (of active ingredient). For most economical and effective use the dusts can be applied in bands of 6 to 8 inches centered on the rows just prior to seeding. The material can then be rototilled to a depth of several inches. This mode of treatment saves material and protects the root system of young plants against microbial attack. For the protection of a given crop, such as cabbage, the band spread of antimicrobial can vary from 8 inches for black root disease to 12–15 inches for club root disease prevention. Similarly, the depth to which the fungicide should be distributed can vary from 2 to 6 inches.

The wettable powders can be prepared by the addition of 0.15% of a wetting agent to the powder blends.

Many dispersing agents are commercially available which are nonphytotoxic at the required concentrations. These may, for example, be alkali metal and amine salts of sulfated and sulfonated acids, alcohols, and oils, or polyethoxylated alkyl phenols, long chain fatty amine quaternary salts, partial phenols, partial fatty acid esters of polyhydric alcohols, etc. Some dispersants can be used in preparing emulsifiable concentrates of the polyamines in organic solvents. Many of these agents are available in solvent-soluble form. The manner of application to the soil is similar to the dusts. Spray equipment is used to spread the suspensions or emulsions over the soil and by discing, the fungicidal agents can be uniformly distributed to varying depths. Spray application is also effective for band-limiting the dosages.

Other agricultural uses for these formulations are by application to the phytopathogen involved foliar surface areas. The compounds of this invention show high orders of bacterial inhibition and are especially useful for this purpose. Some of the diseases which are of commercial importance in decreasing yield and quality and are controlled by the compositions of the invention are fire blight of apple and pear, bacterial spot on stone fruit, cherry leaf spot, walnut blight, common blight of bean, bacterial spot of tomato and pepper, and potato seed piece decay. The effective concentration of 2,4-di-substituted-1,2,5-thiadiazol-3(2H)-one required varies from 5–200 parts per million parts. They may be applied as dusts, powder dispersions in water, as emulsions in water, or as aqueous dipping baths. Other plant diseases which can be controlled by treatment with these formulations are fungal in origin, such as the many kinds of powdery mildew and leaf scabs.

For seed treatment, proportions as low as 1 to 4 ounces per hundred weight (550 to 600 ppm on seed) are effective against various fungi.

The compounds of the invention can be used in form of aqueous suspensions or emulsions, the base products being generally insoluble in water. For this type of formulation various powdered carriers can be employed to aid in achieving uniform distribution. Talc, fuller's earth, calcium silicate, calcium carbonate, clays and the like are admixed with the agent along with wetting and dispersing agents and sticking agents. For maximum chemical compatability those which are nonionic in character are preferred. Other nonionic or cationic surfactants are also satisfactory.

What is claimed is:
1. A compound of the formula:

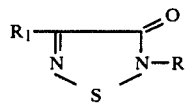

where R is $C_1$ to $C_{18}$ alkyl linear or branched; phenyl —$C_1$ to $C_{10}$ alkyl, phenyl, and phenyl independently mono- or di-substituted with bromine, chlorine, fluorine and iodine, alkyl containing from $C_1$ to $C_{12}$ carbon atoms or alkoxy having the same number of carbon atoms; and $R^1$ is $C_1$ to $C_{18}$ alkyl, linear or branched; loweralkoxyalkyl wherein the alkoxy group contains from one to six carbon atoms and the alkyl moiety from one to four carbon atoms, tetrahydrofuran-2-ylmethyl, and phenyl-$C_1$ to $C_{10}$ alkyl; ring substituted or disubstituted phenyl $C_1$ to $C_{10}$ alkyl where said substituent is the same or different and said substituent is bromine, chlorine, fluorine or iodine, $C_1$ to $C_{12}$ alkyl or $C_1$ to $C_{12}$ alkoxy.

2. A compound according to claim 1 where R is $C_1$ to $C_{18}$ alkyl.

3. A compound according to claim 1 where R is phenyl $C_1$ to $C_{10}$ alkyl, linear or branched.

4. A compound according to claim 1 where R is phenyl.

5. A compound according to claim 1 wherein $R^1$ is $C_1$ to $C_{18}$ alkyl.

6. A compound selected from the group consisting of:
2-(4-Chlorophenylmethyl)-4-methyl-1,2,5-thiadiazol-3-one
2-(3,4-Dichlorophenylmethyl-4-methyl-1,2,5-thiadiazol-3-one
2-Phenyl-4-methyl-1,2,5-thiadiazol-3-one
2-n-Hexyl-4-methyl-1,2,5-thiadiazol-3-one
2-n-Propyl-4-(phenylmethyl)-1,2,5-thiadiazol-3-one
2-n-Propyl-4-(4-chlorophenylmethyl)-1,2,5-thiadiazol-3-one
2-n-Propyl-4-(3,4-Dichlorophenylmethyl)-1,2,5-thiadiazol-3-one
2-(4-Chlorophenyl)-4-methyl-1,2,5-thiadiazol-3-one
2-(4-Chlorophenylmethyl-4-(tetrahydrofuran-2-ylmethyl)-1,2,5-thiadiazolone

* * * * *